(12) United States Patent
Redmond et al.

(10) Patent No.: US 7,914,817 B2
(45) Date of Patent: Mar. 29, 2011

(54) TREATMENT OF INFLAMMATORY BOWEL DISEASE

(75) Inventors: H. Paul Redmond, Wilton (IE); Rolf W. Pfirrmann, Lucerne (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 486 days.

(21) Appl. No.: 11/039,958

(22) Filed: Jan. 24, 2005

(65) Prior Publication Data

US 2005/0124609 A1    Jun. 9, 2005

Related U.S. Application Data

(63) Continuation of application No. 10/322,747, filed on Dec. 19, 2002, now abandoned, which is a continuation of application No. 09/753,679, filed on Jan. 4, 2001, now abandoned.

(60) Provisional application No. 60/174,608, filed on Jan. 5, 2000.

(51) Int. Cl.
*A61K 9/20* (2006.01)
*A61K 9/22* (2006.01)
*A61K 9/28* (2006.01)

(52) U.S. Cl. .................. 424/464; 424/468; 424/474
(58) Field of Classification Search .................. 424/464
See application file for complete search history.

(56) References Cited

U.S. PATENT DOCUMENTS

| | | | |
|---|---|---|---|
| 3,423,408 A | | 1/1969 | Pfirrmann |
| 4,022,889 A | | 5/1977 | Bannister |
| 4,096,241 A | | 6/1978 | Geistlich et al. |
| 4,107,305 A | | 8/1978 | Pfirrmann |
| 4,337,251 A | | 6/1982 | Pfirrmann |
| 4,587,268 A | | 5/1986 | Pfirrmann |
| 4,604,391 A | | 8/1986 | Pfirrmann |
| 4,626,536 A | | 12/1986 | Pfirrmann |
| 4,772,468 A | | 9/1988 | Pfirrmann |
| 4,882,149 A | | 11/1989 | Spector |
| 4,960,415 A | | 10/1990 | Reinmüller |
| 5,077,281 A | * | 12/1991 | Reinmuller |
| 5,187,082 A | | 2/1993 | Hamill et al. |
| 5,210,083 A | * | 5/1993 | Pfirrmann |
| 5,256,684 A | | 10/1993 | Marshall |
| 5,304,540 A | | 4/1994 | Blackburn et al. |
| 5,316,774 A | | 5/1994 | Eury et al. |
| 5,417,975 A | | 5/1995 | Lussi et al. |
| 5,559,096 A | | 9/1996 | Edwards et al. |
| 5,591,714 A | | 1/1997 | Nagarajan et al. |
| 5,593,665 A | | 1/1997 | Pfirrmann |
| 5,599,794 A | | 2/1997 | Eek et al. |
| 5,650,320 A | | 7/1997 | Caufield et al. |
| 5,972,933 A | * | 10/1999 | Pfirrmann |
| 6,251,896 B1 | * | 6/2001 | Costin |

FOREIGN PATENT DOCUMENTS

| | | |
|---|---|---|
| WO | WO 90/06138 A1 | 6/1990 |
| WO | WO 91/04732 A1 | 4/1991 |
| WO | WO 91/13628 A1 | 9/1991 |
| WO | 9725980 * | 7/1997 |
| WO | WO 97/25980 A1 | 7/1997 |
| WO | WO 97/27843 A2 | 8/1997 |

OTHER PUBLICATIONS

"5-ASA (mesalamine) oral medications", MedicineNet.com, Nov. 24, 2008, 5 pages.
"Ibuprofen", Wikipedia.org, Nov. 24, 2008, 8 pages.
Drygalski, et al., "Vancomycin-Induced Immune Thrombocytopenia", The New England Journal of Medicine, vol. 356:904-910, Mar. 1, 2007, No. 9, 10 pages.
"Vancomycin", Drugs.com, Dec. 3, 2008, 3 pages.
Pravda, "Radical induction theory of ulcerative colitis", World Journal of Gastroenterology, vol. 11, No. 16, Apr. 28, 2005, ISSN 1007-9327, pp. 2371-2384.
Dickinson, et al., "Double blind controlled trial of oral vancomycin as adjunctive treatment in acute exacerbations of idiopathic colitis", Gut, 1985; 26, pp. 1380-1384.
Chapman, et al., "Controlled trial of intravenous metronidazole as an adjunct to corticosteroids in severe ulcerative colitis", Gut, 1986:27, pp. 1210-1212.
Gardiner, K.R. et al., "Enteral and Parenteral Anti-Endotoxin Treatment in Experimental Colitis" Hepato-Gastroenterology, vol. 41, No. 6, 1994, pp. 554-558, Northern Ireland.
Johnston, D.A. et al., "Taurolin for the prevention of parenteral nutrition related infection: antimicrobial activity and long-term use" Clinical Nutrition, vol. 12, No. 6, Dec. 1, 1993, pp. 365-368, London, England.
Baert, F.J. et al., "Anti-TNF strategies in Crohn's disease: mechanisms, clinical effects, indications" Int'l. Journal of Colorectal Disease, vol. 14, No. 1, Feb. 1999, pp. 47-51, Berlin, Germany.
J.A.F. Reynolds Editor, "Martindale—The Extra Pharmacopoeia—30th Ed." 1993, The Pharmaceutical Press, p. 211, middle column, paragraph 2, London, England.
Vincent, Jean-Louis, "Dear SIRS, I'm sorry to say that I don't like you . . . ", Crit. Care Med., 1997, vol. 25, No. 2, pp. 372-374.
Bone, R.C., "Sepsis and Septic Shock", Consultant Series (3) No. 2, pp. 1-3 and 5-25 (1987).

(Continued)

*Primary Examiner* — Humera N Sheikh
(74) *Attorney, Agent, or Firm* — Rothwell, Figg, Ernst & Manbeck, P.C.

(57) ABSTRACT

Patients suffering from inflammatory bowel disease such as Crohn's disease or ulcerative colitis are treated either orally or intravenously with methylol transfer agents, such as taurolidine and/or taurultam. These agents can be used in combination with other drugs thereby allowing the use of smaller amounts of the other drugs and limiting unwanted side effects.

7 Claims, No Drawings

OTHER PUBLICATIONS

Stinson, S., "Drug Firms Restock Antibacterial Arsenal", *Product Report*, Sep. 23, 1996, C&EN.

Rampp, U., "Medizin Im Dialog", Aug. 1996 (untranslated), pp. 1-27.

Traub, W. et al., "Enterococcus faecium: In vitro Activity of Antimicrobial Drugs, Singly and Combined, with and without Defibrinated Human Blood, against Multiple-Antibiotic-Resistant Strains", *Chemotherapy*, 1993, vol. 39, pp. 254-264.

Browne, M.K. et al., "The in Vitro and in Vivo Activity of Taurolin Against Anaerobic Pathogenic Organisms", *Surgery, Gynecology & Obstetrics*, 1977, vol. 145, pp. 842-846.

Willatts, S. et al., "Effect of the Antiendotoxic Agent, Taurolidine, in the Treatment of Sepsis Syndrome: A Placebo-Controlled Double-Blind Trial", *Critical Care Med.*, 1995, vol. 23, No. 6, pp. 1033-1039.

Jones, D.S. et al., The Effects of Three Non-Antibiotic, Antimicrobial Agents on the Surface Hydrophobicity of Certain Micro-Organisms Evaluated by Different Methods, *J. Appl. Bacteriol.*, 1991, vol. 71, pp. 218-227.

Hancock, R., "Peptide Antibiotics", *The Lancet*, 1997, vol. 349, pp. 418-422.

Zimmerman, M. et al., "In Vitro Activity of Taurolidine, Chlorophenol-Camphor-Menthol and Chlorhexidine Against Oral Pathogenic Microorganisms", *Arzneim-Forsch/Drug Res.*, 1992, vol. 42(II), pp. 1157-1159.

Focht, J. et al., "Spectrum of Pathogens and Resistance in Peritonitis", *Langebecks Arch Chir.*, 1997, vol. 382 (suppl 1), S1-S4.

Vankemmel, M. et al., "Traitement Anti-Infectieux Local et General Par Utilisation D'un Nouvel Antiseptique en Chirurgie Bilio-Pancreatique: Un Defi Ax Antibiotiques?", *Med Interne*, 1979, vol. 14, No. 12, pp. 683-688 (untranslated).

Ruegsegger, C.H. et al., "Tauroline in Intra-Abdominal Infections", *Helv. Chir. Acta.*, 1978, vol. 45, No. 6, pp. 743-747 (untranslated).

Ruegsegger, C.H. et al., "Comparative Study on Prophylactic Antibiotics Versus Perioperative Taurolidine in Colonic Surgery", *Helv. Chir. Acta.*, 1983, vol. 50, pp. 117-120 (untranslated).

Rosman, C., et al., "Effect of Intraperitonial Antimicrobials on the Concentration of Bacteria, Endotoxin, and Tumor Necrosis Factor in Abdominal Fluid and Plasma in Rats", *Eur. Surg. Res.*, 1996, vol. 28, No. 5, pp. 351-360.

Gortz, G., "Local Antiseptic and Antiendotoxic Measures in the case of Intraabdominal Infections", *Langenbecks Archiv Für Chirurgie*, 1997, vol. 382 (Suppl 1), S.37-S41.

Linder, M. et al., "Therapy of Purulent Peritonitis", *Langenbecks, Arch Chir.*, 1981, vol. 353, No. 4, pp. 241-250.

Brown, M, The Treatment of Peritonitis by an Antiseptic—Tauroline, *Pharmatherapeutica*, 1981, vol. 2, No. 8, pp. 517-522.

Traub, Wh. et al., "Taurolidine: In Vitro Activity Against Multiple-Antibiotic-Resistant, Nosocomially Significant Clinical Isolates of Staphylococcus Aureus, Enterococcus Faecium, and Diverse Enterobacteriaceae", *Chemotherapy*, 1993, vol. 39 (5).

Tarao, M. et al., "Effect of Paromomycin Sulfate on Endotoxemia in Patients with Cirrhosis", *J. Clin Gastroenterol*, 1982, vol. 4 (3).

Krawzak, H.W., et al., "Taurolinein the Local Treatment of Peritonitis", *Aktuel. Chir.*, 1987, Abstract.

Reith, HB, et al., "Peritonitis Therapy Today: Surgical Management and Adjuvant Medical Therapies", *Langenbecks Archiv. Fur Chirurgie*, 1997, vol. 382 (4 Suppl. 1), Abstract.

Lai, K et al., "35th Interscience Conference on Antimicrobial Agents and Chemotherapy", *Abstracts of the 35th ICAAC*, Abstract (1995).

* cited by examiner

TREATMENT OF INFLAMMATORY BOWEL DISEASE

The present application is a continuation of application Ser. No. 10/322,747, filed Dec. 19, 2002, which is a continuation of application Ser. No. 09/753,679, filed Jan. 4, 2001, which claims the benefit of U.S. Provisional Application No. 60/174,608, filed Jan. 5, 2000.

BACKGROUND OF THE INVENTION

Inflammatory bowel disease (IBD) is of unknown etiology, although immunological mechanisms play a significant role. The two major disorders involved are ulcerative colitis and Crohn's disease. Both diseases are chronic relapsing disorders.

The exact pathogenesis of IBD is unknown. Various factors such as environmental, genetic, smoking and infectious agents have been suggested.

IBD is characterized by a chronic remitting and relapsing course. The general aims of treatment are to induce remission and prevent relapse. The approach to therapy varies according to type, distribution and severity of disease in individual patients.

Current therapies for IBD include anti-inflammatories and steroids and sulphasalazine. Immunosuppressive agents such as azathioprine, 6-mercaptopurine, cyclosporin and methotrexate are emerging as potentially useful agents in severe and refractory cases of IBD. Other treatment modalities undergoing investigation include lipoxygenase inhibitors, fish oil and hydroxychloroquinine.

Exacerbation of inflammatory bowel disease, ulcerative colitis and Crohn's disease, is marked by local release of proinflammatory mediators, increased vascular permeability, and recruitment of acute inflammatory cells, which ultimately leads to mucosal ulceration. It has been shown that proinflammatory cytokines such as tumor necrosis factor-$\alpha$ (TNF-$\alpha$), interleukin-1$\beta$ (IL-1$\beta$) and interleukin-6 (IL-6) tend to be consistently elevated in patients with active IBD. Furthermore, increased levels of angiogenic cytokines such as vascular endothelial growth factor (VEGF) has been recently demonstrated in patients with IBD. Peripheral monocytes and intestinal macrophages from patients with IBD have been found with an enhanced ability to secrete increased amounts of proinflammatory cytokines. An increased capacity to secrete IL-1$\beta$ and TNF-$\alpha$, two proinflammatory cytokines particularly important for inducing and sustaining intestinal inflammation in IBD, has been found in polymorphonuclear neutrophil granulocytes (PMN) from patients with active IBD. Reactive oxygen species and nitric oxide mainly released from PMN in patients with IBD have been considered as important factors in the pathogenesis of IBD. It is now becoming clear that inflammatory cells and monocyte- and PMN-released mediators may play a key role in the amplification of inflammation and tissue damage in IBD.

Lipopolysaccharide (LPS) or endotoxin comprises the key element of most gram-negative and some gram-positive bacteria. LPS is an important mediator of gram-negative sepsis and septic shock. LPS itself has been implicated as one of the potent. inducers of proinflammatory mediator synthesis and release, including cytokines and reactive oxygen metabolites in inflammatory cells. Endotoxemia may occur in the absence of gram-negative bacteremia because endotoxin can transit the normal gut wall in small amounts. Such transiting of endotoxin is potentially increased by the presence of mucosal inflammation in patients with active IBD, which eventually leads to endotoxemia.

SUMMARY OF THE INVENTION

In accordance with the present invention, a method of treating inflammatory bowel disease in a patient comprises administering to the patient an effective amount of a methylol transfer agent.

DETAILED DESCRIPTION OF THE INVENTION

Without being bound to any particular theory, it is believed that block of endotoxin both systematically and locally may have beneficial effect on IBD through inhibition of inflammatory cell activation and reduction of proinflammatory mediator release. Taurolidine is a proven chemotherapeutic agent with a potent bactericidal and antiendotoxih effect. Its mechanism of action, unlike that of antibiotics, is based on a chemical reaction. During the metabolism of taurolidine to taurinamide and ultimately taurine and water, methylol groups are liberated and chemically. react with the mureins in the bacterial cell wall and the amino and hydroxyl groups of endotoxin and exotoxins. This results in denaturing of the complex polysaccharide and lipopolysaccharide components of the bacterial cell wall and endotoxin and in the inactivation of susceptible exotoxins.

The present invention is applicable to any suitable methylol transfer agent that reduces inflammatory bowel disease in a patient. Although the invention is further described with respect to the methylol transfer agents taurolidine and/or taurultam, it is to be understood that the invention is equally applicable to any suitable methylol transfer agent having activity similar to or substantially the same as taurolidine and/or taurultam.

Methylol transfer agents in accordance with the present invention can be administered in any suitable form, such as orally administered tablets or capsules, or intravenously administered solutions.

Taurolidine (bis(1,1-dioxoperhydro-1,2,4-thiadiazin-4-yl) methane) has been employed as a clinically effective therapeutic agent for many years. The compounds taurolidine and taurultam are as disclosed in U.S. Pat. No. 5,210,083, incorporated herein by reference. Taurolidine has been utilized both for antibacterial prophylaxis and as a therapeutic bactericidal agent in peritoneal sepsis. It has a short half life and is rapidly metabolized to taurine, carbon dioxide and water. Taurolidine has been shown to have a broad spectrum of antimicrobial activity against both gram positive and gram negative bacteria and fungi and has a neutralizing activity against bacterial endotoxin. Taurolidine has been shown to be non-toxic to humans and animals and is free from side effects following intravenous and intraperitoneal administration. This wide spectrum of antiseptic properties has led to its clinical application in conditions ranging from osteomyelitis to peritonitis and catheter related sepsis prophylaxis.

The use of methylol transfer agents in IBD may be based on their specific modes of action. These include: 1) Reduction/inhibition of the inflammatory reaction, 2) Selective destruction of pathogenic bacteria, and 3) Protection of epithelial cells in the gut wall.

Preferred dosages contain about 100-1000 mg taurolidine and/or taurultam, most preferably about 200-500 mg thereof. Dosages may be administered 1, 2, 3, 4, 5 or more times per day, preferably on a daily basis.

Administration of taurolidine together with known IBD treatment agents could allow the use of lower amounts of the other agents, e.g., using taurolidine in combination with Remicade for treating Crohn's disease could allow the use of lower amounts of Remicade. The use of taurolidine to decrease the necessary levels of other drugs will decrease any deleterious side effects which may be associated with use of the higher levels of those other agents.

The present invention may be applicable, inter alia, to: A) Patients with Crohn's disease active and inactive the effectiveness of which can be measured by using the Crohn's disease activity index (CDAI); and B) Patients with ulcerative colitis active and inactive, the effectiveness of which can be measured by using the clinical colitis activity index (CAI).

According to one embodiment, patients receive a single oral dose of 20 g taurolidine suspension per day for ten days.

The present invention is described by reference to the following Examples, which are offered by way of illustration and are not intended to limit the invention in any manner. Standard techniques well known in the art or the techniques specifically described below were utilized.

EXAMPLE 1

This experiment evaluates the beneficial effects of oral administration of taurolidine on attenuation of systemic inflammatory response in patients with active inflammatory bowel disease. This Example measures systemic proinflammatory and angiogenic cytokines, systemic reactive oxygen species and nitric oxide in patients with IBD pre- and post-taurolidine administration. Secondly, circulating PMN and monocytes from patients with IBD are assessed for their adhesion receptor expression, and their ability to release proinflammatory and angiogenic cytokines, as well as reactive oxygen species and nitric oxide following taurolidine treatment.

A) Experimental Design
1) Peripheral venous blood samples are collected from patients on the day before taurolidine administration, and day 2, day 5 and day 10 after taurolidine administration. Serum samples are harvested by centrifugation and stored at −80° C. for measurement of serum levels of endotoxin, LPS binding protein (LBP), and soluble CD14, serum proinflammatory cytokines (TNF-α, IL-1β, IL-6), serum angiogenic cytokines (VEGF, TGF-β1), serum lipid peroxides (malonaldehyde), nitric oxide and peroxynitrite.
2) Receptor expression of CD11a, CD11b, CD18, and CD14 on PMN and monocytes in the whole blood samples are assessed on the day before taurolidine administration, and day 2, day 5, and day 10 after taurolidine administration. PMN respiratory burst and phagocytosis in the whole blood samples are examined at different time points pre- and post-taurolidine administration.
3) Circulating PMN and monocytes are isolated from patients on the day before taurolidine administration, and day 5 and day 10 after taurolidine administration using the Dextran-Ficoll density gradient technique. Isolated PMN and monocytes will be assessed for their spontaneous and LPS-stimulated proinflammatory cytokine release and for angiogenic cytokine release.
4) Clinical symptoms and signs in patients with IBD are examined on the day before taurolidine administration, and day 5 and day 10 after taurolidine administration.

B) Methodology
Dextran-Ficoll gradient sedimentation for circulating PMN isolation; solid-phase ELISA for assessment of proinflammatory cytokines, angiogenic cytokines, serum LBP and soluble CD14; flow cytometry for determination of PMN and monocyte receptor expression, respiratory burst and phagocytosis; Limulus amebocyte lysate assay for detection of serum endotoxin levels; colorimetric assay for determination of lipid peroxidation; fluorescent probe DHR 123 and Greiss reaction for measurement of peroxynitrite and nitric oxide, are utilized respectively.

C) Results
There are increased systemic proinflammatory and angiogenic cytokine levels, and increased PMN and monocyte adhesion receptor expression in patients with active IBD. Systemic lipid peroxides, nitric oxide and peroxynitrite also are increased with enhanced potential of PMN and monocytes to release proinflammatory and angiogenic cytokines, as well as reactive oxygen species in patients with active IBD. Administration of taurolidine ameliorates these phenomena in patients with IBD.

EXAMPLE 2

This example evaluates the beneficial effect of oral administration of taurolidine on amelioration of inflammatory response in intestinal mucosa in patients with active inflammatory bowel disease. This Example measures proinflammatory cytokines, angiogenic cytokines, reactive oxygen species and nitric oxide in the mucosal biopsy cultures in patients with IBD pre- and post-taurolidine administration. Local mucosal recruited PMN and mononuclear leukocyte-associated proinflammatory cytokine and angiogenic cytokine expression in patients with IBD are assessed pre- and post-taurolidine treatment.

A) Experimental Design
1) The specimens of standard intestinal mucosal biopsy are collected from patients with IBD on the day before taurolidine administration, and day 5 and day 10 after taurolidine administration, and incubated with completed culture medium for different time points. The supernatants from the biopsy cultures are harvested by centrifugation and stored at −80° C. for measurement of proinflammatory cytokines (TNF-α, IL-1β, IL-6), angiogenic cytokines (VEGF, TGF-β1), lipid peroxides (malonaldehyde), nitric oxide and peroxynitrite.
2) The mononuclear leukocytes from the above specimens of mucosal biopsy are isolated using the technique of collagenase-digestion and density gradient sedimentation. TNF-α, IL-1β, IL-6 and VEGF protein and mRNA expression in these mononuclear leukocytes are assessed.
3) The specimens of standard intestinal mucosal biopsy from patients with IBD on the day before taurolidine administration, and day 5 and day 10 after taurolidine administration are assessed for PMN- and monocyte-associated TNF-α, IL-1β, IL-6 and VEGF expression.
4) Pathological changes of intestinal mucosa in patients with IBD are examined on the day before taurolidine administration, and day 5 and day 10 after taurolidine administration.

B) Methodology
Collagenase digestion and Percol gradient sedimentation for isolation of mucosa-associated mononuclear leukocytes; solid-phase ELISA for assessment of TNF-α, IL-1β, IL-6, VEGF and TGF-β1 in supernatants from the biopsy cultures; flow cytometry and RT-PCR for determination of intracellular TNF-α, IL-1β, IL-6 and VEGF protein expression and mRNA expression in mucosa-associated mononuclear leukocytes, respectively; colorimetric assay for determination of lipid peroxidation; fluorescent probe DHR 123 and Greiss reaction for measurement of peroxynitrite and nitric oxide, respectively; immunocytochemistry for detection of PMN- and monocyte-associated TNF-α, IL-1β, IL-6 and VEGF expression in mucosal biopsy specimens, are utilized.

C) Results

Patients with active Crohn's disease and active ulcerative colitis have increased levels of proinflammatory cytokines, angiogenic cytokines, and reactive oxygen species, which is related to the increased recruited PMN and monocytes in intestinal mucosa. Treatment with taurolidine improves pathological changes in intestinal mucosa in patients with active IBD, which is associated with downregulation of proinflammatory cytokines, angiogenic cytokines, reactive oxygen species, and recruitment of PMN and mononuclear leukocytes in the intestinal mucosa by taurolidine.

The above Examples are repeated using intravenous administration of taurolidine. Examples of the tablets to be utilized or the intravenous formulations to be used are described in the following Examples.

EXAMPLE 3

Tablets with Gastric Juice Resistant Coating Soluble in the Bowel

Tablets comprising 200 mg taurolidine with a total tablet weight of approximately 460 mg, a diameter of 11 mm and a thickness of 4 mm were prepared. Each tablet comprises:

| Component | Name | Amount |
|---|---|---|
| 1 | Taurolidine | 200 mg |
| 2 | Emdex ® (Penwest Pharm. co., NY, USA) | 100 mg (Dextrates, NF hydrated) |
| 3 | Starch 1500 | 100 mg |
| 4 | Talcum | 8 mg |
| 5 | Mg-stearate | 1 mg |
| 6 | Aerosil 200 | 1 mg |

To manufacture the tablets, the components are mixed in a stainless steel container and rotated on a Rhoen-wheel or in a stainless steel mixing machine. Components 1-3 are preliminarily mixed for approximately 10 minutes. Thereafter, components 4-6 are added and mixed for another 10 minutes. Formation of the tablets is on an excenter-tablet press.

Coating of the tablets is performed in a coating pan with a gastric juice resistant coat on the basis of an acrylic resin, using the Eudragit® types of Rhön Pharma GmbH, D-Darmstadt, Germany. Coating is effected under slow rotation with a spray system using a solution of Eudragit® L30D (Poly[meth]acrylic acid ester, MW 800,000) in an isopropyl-alcohol:water mixture of 70:30. Alternatively, Eudragit® EL may be used for the coating.

Varnishing is effected by a 12.5% solution in isopropyl-alcohol. Thereafter the coated/vanished tablets are dried in a vacuum-drying oven.

EXAMPLE 4

Tablets with Gastric Juice Resistant Coating Soluble in the Bowel

Tablets are prepared as in Example 3 except 200 mg taurultam are used in place of the 200 mg taurolidine.

EXAMPLE 5

Tablets with Gastric Juice Resistant Coating Soluble in the Bowel

Tablets are prepared as in Example 3 except that in place of 200 mg taurolidine, the tablets comprise 100 mg taurolidine and 100 mg taurultam.

EXAMPLE 6

Slow Intravenous Drop Infusion—I.V. Infusion Solution for Crohn's Disease

An intravenous solution for administration via a central catheter or port is prepared in volumes of 100, 250 or 500 mL with taurolidine at 2% in glass bottles of 100, 250 or 500 mL with rubber stoppers and aluminum caps.

| Component | Name | Amount |
|---|---|---|
| 1 | Taurolidine | 1 g |
| 2 | Taurultam | 1 g |
| 3 | Povidone UP | 5 g (see U.S. Pat. No. 6,080,397) |
| 4 | Sterile water | to 100 mL | pH after sterilization is 7.2-7.3.

EXAMPLE 7

Slow Intravenous DroD Infusion—I.V. Infusion Solution for Crohn's Disease

An intravenous solution for administration via central catheter or port is prepared as in Example 6 but with the following:

| Component | Name | Amount |
|---|---|---|
| 1 | Taurolidine | 20 g |
| 2 | Povidone UP | 50 g (see U.S. Pat. No. 6,080,397) |
| 3 | D-glucosemonohydrate | 10 g |
| 4 | Sterile water | to 1000 mL | pH after sterilization is 6.8.

EXAMPLE 8

Administration of Taurolidine to Patients with Inflammatory Bowel Disease

Four patients with inflammatory bowel disease were treated daily with orally administered 300 mg taurolidine capsules.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method of treating ulcerative colitis or Crohn's disease in a patient comprising orally administering to said patient an effective amount of a methylol transfer agent having activity substantially the same as taurolidine or taurultum, wherein said methylol transfer agent is administered to said patient at an oral dose of about 100-1000 mg.

2. The method of claim 1 wherein said agent is selected from the group consisting of taurolidine, taurultam, and mixtures thereof.

3. The method of claim 2, wherein taurolidine is administered to said patient at an oral dose of about 100-1000 mg.

4. The method of claim 3 wherein said taurolidine is administered to said patient daily.

5. The method of claim 4 wherein about 20 g of said taurolidine is administered to said patient daily.

6. The method of claim 1 wherein said agent is further administered intravenously to said patient.

7. The method of claim 1 wherein infliximab in addition to said methylol transfer agent is administered to said patient.

* * * * *